United States Patent [19]

Ores

[11] 4,427,684
[45] Jan. 24, 1984

[54] TREATMENT AND PREVENTION OF INFECTION WITH HERPES SIMPLEX AND RELATED VIRUSES

[76] Inventor: Richard O. Ores, 194 Larch Ave., Teaneck, N.J. 07666

[21] Appl. No.: 423,233

[22] Filed: Sep. 24, 1982

[51] Int. Cl.³ .............................................. A61K 31/445
[52] U.S. Cl. .................................................... 424/267
[58] Field of Search .......................................... 424/267

[56] References Cited

PUBLICATIONS

Bauer et al., Chemotherapy of Virus Diseases, vol. 1, Dergamow Press, N.Y., N.Y., Mar. 1973, p. 9.

Primary Examiner—Jerome D. Goldberg
Attorney, Agent, or Firm—Ostrolenk, Faber, Gerb & Soffen

[57] ABSTRACT

Cycloheximide is used in the treatment as well as prophylaxis of infection caused by herpes simplex hominis and related viruses.

9 Claims, No Drawings

TREATMENT AND PREVENTION OF INFECTION WITH HERPES SIMPLEX AND RELATED VIRUSES

BACKGROUND OF THE INVENTION

Herpes simplex is an infection caused by herpes hominis simplex Type I and II. The virus attacks the skin and/or mucous membranes before the lesion becomes visible. The first signs consist of mild parasthesia, burning sensation and itching or pain locally. Once the lesions develop, headaches, general malaise and low grade fever are common. This is followed by the appearance of small red papules that soon change to fluid filled blisters on the skin or mucous membranes which dry out within several weeks, scab and heal but tend to recur over and over again.

There are two types of herpes simplex. Type I is known as the skin or "above the umbilicus" virus that causes fever blisters, and type II is known as the "below the umbilicus" virus responsible for genital infections. The two types can be distinguished by serologic examination of the antibodies produced after exposure to the virus but cannot be differentiated in a culture. The herpes simplex infections are also named after their localisation, e.g., herpes labialis, occular herpes, herpes genitalis, rectal herpes, herpes digitalis, herpes progenitalis, herpes preputialis, intrauterine herpes, etc. They are aso called herpes febrilis, cold sores, or herpes menstrualis according to timing of their appearance with the above mentioned conditions. Both types of herpes, type I and II, can be sexually transmitted and cause lesions in and on the genitals, on thighs, buttocks, or in the mouth and rectum.

Herpes simplex virus can live for hours outside the human body on a variety of materials and surfaces including toilet seats, plastic containers, specula and gauze as reported by Larson and Bryson, Int. Med. News. 15: 17 (1982). It is actively infective for up to 2½ months in dried crusts from herpetic lesions kept at room temperature as reported by Nahmias et al, "Transport Media for Herpes Simplex Virus Types I and II", Appl. Microbiol. 22: 451–454 (1971). Parvey and Chien, "Neonatal Herpes Virus Infection Introduced by Fetal-monitor Scalp Electrodes", Pediatrics 65: 1150–1153 (1980), described another possibility of non-sexual transmission of herpes simplex infection in an infant who developed acute herpes meningoencephalitis and pneumatosis intestinalis as a result of fetal monitoring with scalp electrodes on the buttocks. The first vesicles appeared at the site where the electrodes were placed. Montefiore et al, "Herpes Virus Hominis type II Infection in Ibadan, Problem of Non-Venereal Transmission", Br. J. Vener Dis. 56: 49–53 (1980), report a possibility of non-venereal transmission of herpes hominis type II that could survive for long enough on cloth samples under humid tropical conditions to cause infections. The herpes simplex hominis virus type I and II are members of a large herpes virus family of which about 70 varieties are known. Those harmful to humans cause birth defects, chicken pox, shingles, mononucleosis and are associated with malignant diseases.

Various treatment of herpes hominis simplex have been proposed. Asculai, U.S. Pat. No. 4,147,803, teaches that certain sorbitan derivatives have anti-herpetic activity. De Long et al., U.S. Pat. No. 3,639,612 described such activity for certain chalcogen containing heterocyclic compounds. Stedman, U.S. Pat. No. 3,555,355, discloses that certain cycloalkylamines have activity against herpes simplex. Fleming et al., U.S. Pat. No. 3,829,578, teaches that certain bis-basic ethers and xanthen-9-ones have anti-viral activity and Soichet, U.S. Pat. No. 4,312,884, describes such antiviral activity by Spectinomycin.

Kaufman et al, Arch. Ophthalmol. 68: 235–239 (1962), reported treatment of herpes simplex keratitis with 5-iodo-2-deoxyridine (IUD). Schabel describes treatment of genital herpetic infection with 9-beta-D-arabino-flurano-syladenine, Chemotherapy 13: 321–338 (1968), and reported antiviral activity of 5-trifluoromethyl-2-deoxyuridine, N.Y. Acad, Sci. 130: 168–180 (1965). Adams et al, J. Infect. Dis. 133 (suppl) 151–159 (1976), treated genital herpes infections with topical application of adenine arabinside. Felber et al, JAMA 223: 289–292 (1973), described treatment of herpes infections by application of a vital dye as neutral red or proflavine followed by exposure to light. Cheseman et al, N. Eng. J. Med. 300: 1345–1349 (1979), and Pazin et al, N. Engl. J. Med. 301: 225–230 (1979), report the treatment of herpes simplex infection by human leukocyte interferon. Blough and Giuntoli, JAMA 241: 2798–2801 (1979), described treatment of human genital herpes infections with 2-deoxy-D-glucose. Schaeffer et al, Nature 272: 583–585 (1978), Fyfe et al, J. Biol. Chem. 253: 8721–8727 (1978), Selby et al, Lancet 2: 1267–1270 (1979), Park et al, J. Infect. Dis. 140: 802–806 (1979), and Pavan-Langston et al, Am. J. Ophthalmol. 86: 618–623 (1978), reported treatment of herpes infections by 9-(2-hydroxyethoxymethyl)guanine (Acyclovir). Fisher, Cutis 29: 467–472 (1982), described treatment of herpes simplex infections with Amantadine hydrochloride. Other forms of treatment of herpes hominis simplex Type I and II include a variety of agents such as lysine, ascorbic acid, topical ether and topical chloroform, tymol, nonionic surfactants, inactivated herpes viruses, zinc, urea, tannic acid, glutaraldehyde, cow pox vaccine, intradermal injections of gamma globulins, and a surgical treatment by epidermal excisions of the herpetic lesions.

It is the object of this invention to provide a new method of treatment and prophylaxis of infections by herpes simplex and related viruses. This and other objects of the invention will become apparent from the following description thereof.

SUMMARY OF THE INVENTION

This invention relates to the treatment of viruses such as herpes simplex, chicken pox, singles and more particularly to the treatment and prevention of infections caused by such viruses as herpes simplex hominis type I and II by administration of cycloheximide.

BRIEF DESCRIPTION OF THE INVENTION

It has been found that cycloheximide is effective in combatting herpes simplex and related herpes infections. Cycloheximide is an antibiotic substance isolated from the beers of Streptomyces griseus cultures. It is 3-2-(3,5-dimethyl-2-oxocyclohexyl)-2-hydroxyethyl glutarimide:

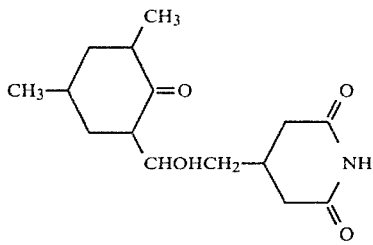

Cycloheximide is commercially available in the United States. Its production, assay and antibiotic activity is described by Whiffen, J. Bacteriol. 56: 283–291 (1948). A trademark name is Actidione. Cycloheximide has been used in treating fungi affecting plants such as golf greens, blue grass, as a control agent against the damping off of alfalfa, or control of covered smut of wheat. Carton, Ann. Intern. Med. 37: 123–154 (1952), used cycloheximide in the systemic treatment of cryptococcosis in humans by intramuscular, intravenous, intrathecal and intraventricular routes without hematologic abnormalities. The only visible toxic type effects were nausea and vomiting. The highest dose given intravenously was 180 mg in a 24 hour period, and 720 mg by intramuscular route per one day. Cycloheximide has also been used in the treatment of experimental Chagas' disease as reported by Packhanian et al, Am. J. Trop. Med. and Hyg. 2: 243–253 (1953), and as a component of mycologic culture medium as described by Georg, Arch. Derm. and Syph. 67: 355–361 (1953). Montes, J. Cut. Pathol. 3: 1–4 (1976), applied cycloheximide topically in the treatment of psoriasis with no signs of skin irritation except for occasional mild temporary erythema.

Cycloheximide inhibits nucleic acid and protein synthesis as reported by Kerridge, J. Gen. Microb. 16: 5 (1957), and by Kleisen and Borst, Biochem. et Biophys. Acta. 390: 78–81 (1975). The inhibition of protein synthesis is also reported by Siegel and Sisler, Bio. Chim, et Biophys. Acta 87: 83–89 (1964), Enis and Lubin, Science 146: 1474–1476 (1964), and Cummins et al, J. Cell Biology 27: 337–342 (1965). Bowen and Wilson, J. of Heredity 45: 3–9 (1955), report the inhibitory effect of cycloheximide on mitosis. The inhibition of DNA synthesis was described by Bennett et al, Bio Chim. et Biophys. Acta 87: 60–82 (1964), and Seki and Mueller, Biochim. et Biophys. Acta 378: 354–362 (1975). Teller and Palm, Amer. Assoc. Canc. Res. Proc. 2: 255 (1957), reported inhibition of the growth of human tumors by cycloheximide.

Iwasaka et al, J. Gen. Virol. 44: 57–67 (1979), described that cycloheximide in a concentration of 10 mug/ml inhibited the appearance of tubular structures, virus particles and the synthesis of virus specific surface antigens in the herpes simplex virus type II infected cultured cells by more than 99%. According to these authors, the appearance of tubular structures is one of the late events in the process of virus multiplication. Oda et al, Arch. Virol. 62: 175–187 (1979), concluded in their study of the tubular structures that these are related to the active production of infectious virus.

It has been found that herpes hominis simplex and other viral infections can be successfully treated by cycloheximide apparently due to its inhibitaion of DNA synthesis and therefore viral reproduction, without serious side effects. Cyclohexamide in a solution can be used for topical treatment such as vaginal douche, oral rinsing solution, and sterilized for parenteral treatment of systemic viral disease or possibly to reach viruses located in the nerve ganglia. The vaginal douche may also be used prophylactically before delivery to prevent neonatal herpetic infections. It can be used in the form of vaginal and rectal suppositories, and as urethral inserts. Convenient form is a dispersion in Aquaphor, an ointment carrier or as an aqueous solution preferably containing a bacteriostatic agent such as benzyl alcohol. Cycloheximide may be also used in combination with other known antibiotics where there is a concomitant secondary bacterial infection. Prophylactically, cycloheximide may be used in solution or spray to prevent a nonvenereal transmission of viral infection. Such compositions can be prepared by standard techniques using standard ingredients. The cycloheximide is effective at concentrations of about 0.05% to 10% or more. The preferred anti-herpetic effective concentration is about 0.1% to 0.2%. A concentration of 0.2% was more effective in the treatment of herpes zoster and chicken pox vesicles. The acute infections are arrested in the first 24 hours and the lesions disappear in the next 72 hours followed by epithelialisation leaving no scarring. Depigmentations were noted after healing of herpes zoster lesions. There was no recurrence of herpes infection in the treated areas but one patient with a history of multiple vaginal lesions developed clusters of herpetic vesicles in the previously not treated areas that responded to treatment and did not reappear again. There were no systemic or local reactions to the treatment observed.

Cycloheximide has been used experimentally to combate herpes hominis simplex, herpes zoster and varicella skin infections. A review of some of these cases is as follows:

Case 1: Female patient, seven months pregnant with a history of recurrent genital herpes in March 1978 (third month of pregnancy) and again in June, 1978 (sixth month) on the major labium. She was told in her maternity clinic that she would have to undergo cesarean section should the herpetic lesion persist. She presented herself with a new lesion in July, 1978. There were several clusters of herpetic vesicles on the inferior medial aspect of the left major labium. She was treated with four applications of 0.2% of cycloheximide in Aquaphor. The lesions subsided and the infected area healed in 5 days. She had an uneventful vaginal delivery on October 18, 1978. The child is normally developed. There has been no recurrence of the herpetic infection until the present time which is four years after the treatment.

Case 2: An 82 year old female with herpes zoster of two days duration. There were clusters of vesicles on left chest from the xyphoid to the vetebral column and complaints of pain. She was treated with six applications of 0.2% cycloheximide in Aquaphor. The lesions healed after one week and the pain subsided. No recurrence until present time.

Case 3: Herpes zoster on the left chest of eight days duration. This individual had been treated previously with 20 mgm prednisone p.o. daily with no improvement. The patient complained of severe local pain related to the area of infection and developed new clusters of vesicles up to 4 mm in diameter. Prednisone was discontinued and a treatment with cycloheximide was started and continued daily until the 16th day after the appearance of the herpetic lesions. The lesions were healed leaving depigmented areas on the 17th day, 9 days after beginning the treatment. There was no recurrence three years after treatment with cycloheximide.

Case 4: Herpetic lesions in the anorectal area of a 59 year old male who had no previous history of herpes simplex infection. Clusters of vesicles in the anal area on the skin and rectal mucosa 1½ cm from the dermomucosal junction. The patient was treated with 0.2% cycloheximide in Aquaphor applied around the anus twice daily and by insertion of gauze saturated with the same ointment into the rectum for about 5 cm depth twice daily for 20 minutes. On the fifth day, the lesions subsided, skin and mucosa healed. There has been no recurrence since treatment 3 years ago.

Case 5: A 42 year old female with herpetic lesions on the lower lip, herpetic vesicles, swelling and pain. She was unable to eat and was receiving liquids through a straw. Twenty-four hours after the beginning of treatment with 0.1% cycloheximide in Aquaphor, the vesicles changed to crusted areas, and the swelling subsided markedly. On the sixth day, the lesions healed completely leaving no scars. No recurrence until present, 3½ years after treatment.

Case 6: Labial herpes of the upper lip of a seventeen year old female who was four months pregnant. The lip was covered with clusters of herpetic vesicles and there was moderate swelling of the lip. She was treated with topical application of 0.1% cycloheximide. There was healing on the 2nd day. The vesicles disappeared leaving clean crusted areas and no swelling. The patient seen on the 8th day after treatment. There was a complete healing with no scarring. She delivered vaginally a normal child in October, 1979, and there has been no recurrence of the herpetic infection.

Case 7: Herpetic infection on the lower lip of a 41 year old woman. The lip was swollen three times its normal size preventing this patient to take solid food. She was fed by straw with liquids. The entire lip and adjacent skin area was covered with vesicles and bloody crusts. The lip and surrounding areas were treated with a thick layer of 0.2% cycloheximide ointment in Aquaphore. The blisters and vesicles subsided after 24 hours leaving clean, punched like areas. The swelling went markedly down. The treatment was performed daily and the lesions healed on the sixth day of treatment. The lip had normal configuration without scarring. No recurrence until present, 3 years later.

Case 8: A 25 year old female with severe multiple recurrent herpetic infection of both major labia in 1979 followed by herpes meningoencephalitis. She presented herself with recurrent herpetic leasions on both labia in June, 1980. The herpetic vesicular lesions that occurred in small clusters subsequently over the period of several months on both labia and preputium of clitoris, but never on the previously treated area, were treated with 0.1% cycloheximide in Aquaphore at the time of the appearance. There was a total of 8 separate lesions treated. All lesions healed without scarring and there was no recurrence of genital herpes until now, 2 years after the last treatment.

Case 9: A 48 year old male with herpetic lesion on the shaft of his penis of 2 days duration. This was a recurrent infection, every few weeks or months for 7 years in the same area. Clusters of vesicles on the dorsum of penis were treated with 0.1% cycloheximide in Aquaphore twice daily for 5 days. Lesions changed to crusted punched like areas in the first 24 hours. There was healing without scaring on the 6th day. No recurrence until present day, 3 years after treatment.

Case 10: A 27 year old woman with herpetic lesion on face, left cheek, consisting of several vesicles surrounded by mild erythema. This lesion appeared for 12 years every spring. There was mild depigmentation measuring 0.3 cm×0.5 cm. She was treated twice daily for six days with 0.2% cycloheximide in Aquaphor. The lesion healed and did not recur in the last two years.

Case 11: Herpetic infection of the right foot involving the dorsal aspect of the distal metatarsal and proximal areas of the first phalanx of the digit I and IV as well as the 3rd phalanx of the digit II and III. Twenty-four hours after treatment with 0.2% cycloheximide in Aquaphor the lesions were clean, and the vesicles subsided as did the swelling. Four days after the beginning of treatment, the lesions were healed without scarring. There was no recurrence one and a half year after the treatment.

Case 12: A 6 year old girl with chicken pox was treated with sponging with 0.1% aqueous solution of cycloheximide twice daily for 7 days. The solution was applied over the body with the exception of the scalp. The vesicular lesions healed in 3 days. The itch and the desire to scratch disappeared and no new vesicles appeared.

Of the first 33 patients who received the cycloheximide treatment, all showed excellent results. No one reported any local or systemic side effects.

Various changes and modifications can be made in the present invention without departing from the spirit and scope thereof. The various embodiments which have been disclosed herein were for the purpose of further illustrating the invention but were not intended to limit it.

What is claimed is:

1. A method of treating herpetic infections which comprises the topical administration of an anti-herpetic effective amount of cycloheximide to an individual in need of such treatment.

2. The method of claim 1 wherein the cycloheximide is administered in combination with an inert carrier therefor.

3. The method of claim 2 wherein the concentration of cycloheximide is about 0.05 to 10%.

4. The method of claim 3 wherein the concentration is about 0.1 to 0.2%.

5. The method of claim 2 wherein the cycloheximide is administered as an ointment.

6. The method of claim 2 wherein the cycloheximide is administered as an aqueous solution.

7. The method of claim 2 wherein the administration is vaginally.

8. The method of claim 2 wherein the administration is rectally.

9. The method of claim 2 wherein the administration is urethrally.

* * * * *